(12) United States Patent
D'Aponte et al.

(10) Patent No.: US 10,894,386 B2
(45) Date of Patent: Jan. 19, 2021

(54) METHOD AND APPARATUS FOR PRODUCING A BREATHABLE WEB AND RELATIVE WEB

(71) Applicant: Fameccanica.Data S.p.A., San Giovanni Teatino (IT)

(72) Inventors: Francesco D'Aponte, Pescara (IT); Serafino Lupinetti, Elice (IT)

(73) Assignee: Fameccanica.Data S.p.A., San Giovanni Teatino (IT)

( * ) Notice: Subject to any disclaimer, the term of this patent is extended or adjusted under 35 U.S.C. 154(b) by 255 days.

(21) Appl. No.: 16/141,610

(22) Filed: Sep. 25, 2018

(65) Prior Publication Data
US 2019/0118509 A1    Apr. 25, 2019

(30) Foreign Application Priority Data
Oct. 20, 2017  (IT) ................. 102017000119053

(51) Int. Cl.
*B32B 37/00* (2006.01)
*B32B 7/05* (2019.01)
(Continued)

(52) U.S. Cl.
CPC .......... *B32B 7/05* (2019.01); *A61F 13/15739* (2013.01); *A61F 13/64* (2013.01); *B29C 65/086* (2013.01); *B29C 65/749* (2013.01); *B29C 65/7457* (2013.01); *B29C 66/0326* (2013.01); *B29C 66/1122* (2013.01); *B29C 66/137* (2013.01); *B29C 66/14* (2013.01); *B29C 66/21* (2013.01); *B29C 66/221* (2013.01);
(Continued)

(58) Field of Classification Search
USPC .......................................... 156/73.1
See application file for complete search history.

(56) References Cited

U.S. PATENT DOCUMENTS

| 4,720,415 A * | 1/1988 | Vander Wielen | ......... B32B 3/28 428/152 |
| 8,679,992 B2 * | 3/2014 | Austin | ...................... B32B 7/08 442/394 |

FOREIGN PATENT DOCUMENTS

| EP | 1355604 A2 | 10/2003 |
| JP | 2008260131 A | 10/2008 |

(Continued)

OTHER PUBLICATIONS

Italian Search Report and Written Opinion dated Jun. 15, 2018 for Application No. IT 201700119053.
(Continued)

*Primary Examiner* — James D Sells
(74) *Attorney, Agent, or Firm* — Patterson + Sheridan, LLP

(57) ABSTRACT

A method for producing a breathable web, comprising: feeding a web on the surface of an anvil roller rotatable about its axis and having a plurality of welding protrusions cooperating with a welding element, welding said web at a plurality of welding spots on head surfaces of said welding protrusions and forming respective annular welding seams at said welding spots, about respective welding projections, and respective thin membranes located within said annular welding seams and adjacent to the head surfaces of said welding protrusions, and removing said thin membranes after said welding by means of a peeling roller having an outer surface tangent to said head surfaces of said welding protrusions.

6 Claims, 5 Drawing Sheets

(51) Int. Cl.
| | |
|---|---|
| *B29C 65/00* | (2006.01) |
| *B29C 65/08* | (2006.01) |
| *A61F 13/15* | (2006.01) |
| *A61F 13/64* | (2006.01) |
| *B29C 65/74* | (2006.01) |
| *B32B 3/26* | (2006.01) |
| *B32B 5/02* | (2006.01) |
| *B32B 27/12* | (2006.01) |
| *B32B 27/32* | (2006.01) |
| *B32B 27/36* | (2006.01) |
| *B32B 37/10* | (2006.01) |
| *B32B 37/20* | (2006.01) |
| *B29L 31/48* | (2006.01) |

(52) U.S. Cl.
CPC .......... *B29C 66/3262* (2013.01); *B29C 66/41* (2013.01); *B29C 66/7294* (2013.01); *B29C 66/7392* (2013.01); *B29C 66/83411* (2013.01); *B29C 66/83511* (2013.01); *B32B 3/266* (2013.01); *B32B 5/022* (2013.01); *B32B 27/12* (2013.01); *B32B 27/32* (2013.01); *B32B 27/36* (2013.01); *B32B 37/0046* (2013.01); *B32B 37/10* (2013.01); *B32B 37/203* (2013.01); *A61F 2013/15869* (2013.01); *B29C 66/71* (2013.01); *B29C 2793/009* (2013.01); *B29C 2793/0018* (2013.01); *B29L 2031/4878* (2013.01); *B32B 2262/0253* (2013.01); *B32B 2262/0276* (2013.01); *B32B 2307/51* (2013.01); *B32B 2307/724* (2013.01); *B32B 2555/02* (2013.01)

(56) References Cited

FOREIGN PATENT DOCUMENTS

| | | |
|---|---|---|
| JP | 2017113187 A | 6/2017 |
| WO | 200145616 A1 | 6/2001 |
| WO | 2012070462 A1 | 5/2012 |
| WO | 2017037617 A1 | 3/2017 |

OTHER PUBLICATIONS

Japanese Office Action dated Oct. 21, 2019, for Japanese Patent Application No. 2018-188804.

* cited by examiner

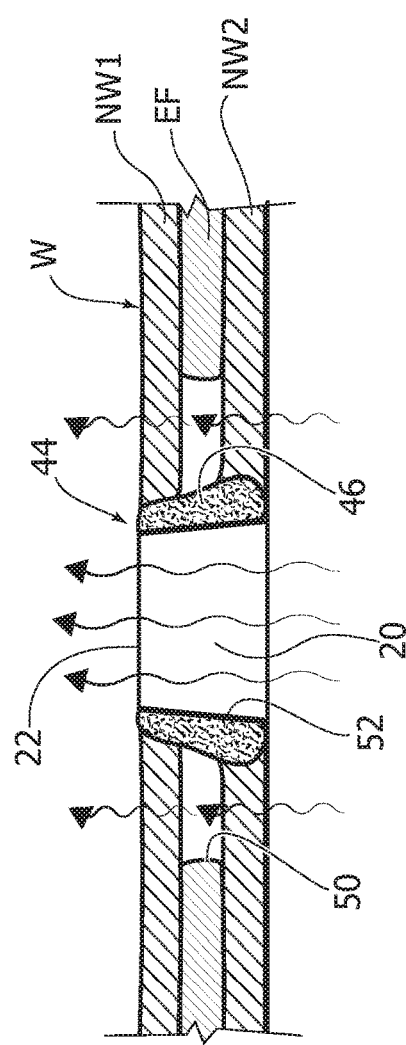
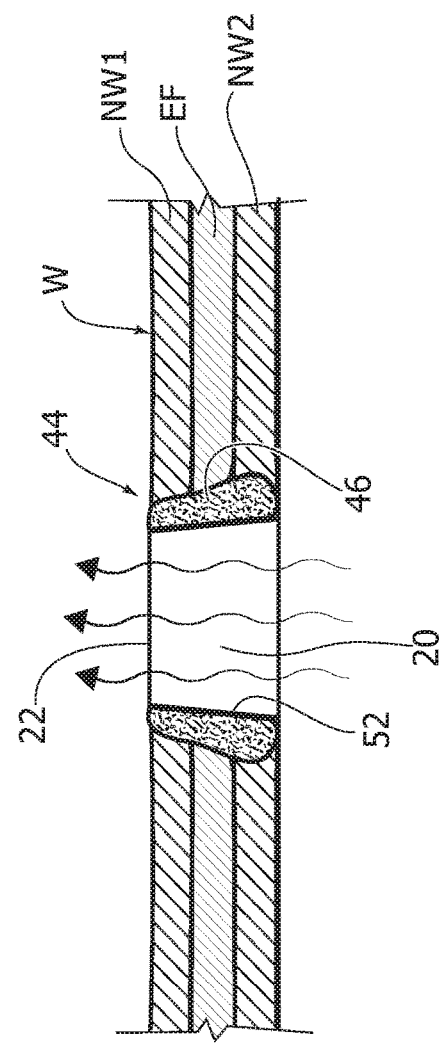

METHOD AND APPARATUS FOR PRODUCING A BREATHABLE WEB AND RELATIVE WEB

CROSS-REFERENCE TO RELATED APPLICATIONS

This application claims benefit of Italian patent application number 102017000119053, filed Oct. 20, 2017 which is herein incorporated by reference.

BACKGROUND OF THE INVENTION

Field of the Invention

The present invention relates to a method and an apparatus for producing a breathable web.

The present invention has been developed, in particular, for producing composite elastic webs intended to be applied in the waist region of disposable absorbent sanitary articles. The scope of the invention is not, however, limited to this possible field of application. For example, the invention can also be applied for producing a single-layered breathable web.

The invention also relates to a breathable web, designed, in particular, to be used for producing disposable absorbent sanitary articles.

Description of Prior Art

The waist regions of disposable absorbent sanitary products are often equipped with elastic webs in order to give the absorbent product better adherence to the user's body. For example, some types of disposable absorbent sanitary products can be formed by two continuous composite elastic webs, parallel to each other and spaced apart from each other in a transverse direction, between which absorbent cores extend transversely with respect to the longitudinal direction of the webs.

A well-established technique for producing elastic webs for absorbent sanitary products involves applying a continuous elastic film in a tensioned state between two layers of non-woven fabric. The two layers of non-woven fabric are generally welded together by means of a welding pattern which comprises a plurality of welding points uniformly distributed on the surface of the composite web.

To improve the comfort of the absorbent sanitary products, it is desirable that the webs forming—for example— the front and back waist bands of the absorbent sanitary products are breathable.

EP-A-1355604 describes an absorbent sanitary product provided with elastic side panels formed by two layers of non-woven fabric between which an elastic film is arranged. The layers of non-woven fabric are welded together by means of ultrasonic welding points. The ultrasonic welding joins the two non-woven layers together, and forms a through-hole through the elastic film and gives the composite web breathability characteristics.

SUMMARY OF THE INVENTION

The present invention aims to provide a method and an apparatus for producing a web that has improved breathability characteristics.

According to the present invention, this object is achieved by a method and an apparatus having the features disclosed herein.

According to another aspect, the object of the invention provides a breathable elastic composite web with improved breathability characteristics.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein:

FIGS. 6, 7 and 8 are greatly enlarged cross-sectional details of the details indicated by arrows VI, VII and VIII in FIG. 1.

FIG. 9 is a cross-section illustrating a variant of FIG. 8.

DETAILED DESCRIPTION

Figure 1:
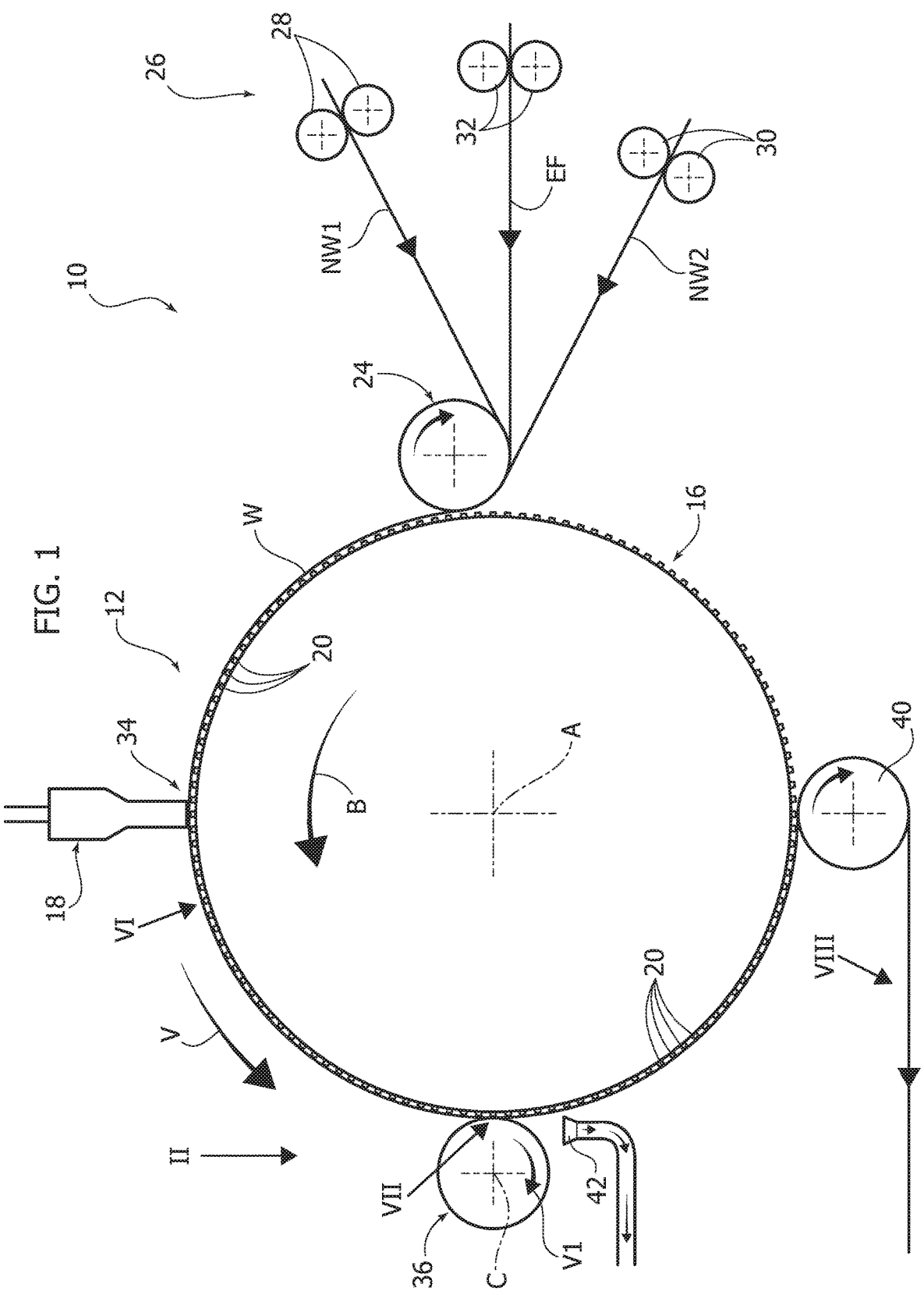
FIG. 1 is a schematic side view illustrating an apparatus for producing a breathable composite elastic web.

With reference to FIG. 1, numeral 10 is a schematic representation of an apparatus for producing a breathable web. The figures illustrate the case in which the apparatus is used for producing a multilayer composite web. However, the apparatus and the method according to the invention can also be used for producing single-layer, elastic or non-elastic breathable webs.

The apparatus 10 comprises a welding unit 12 including an anvil roller 16 rotatable about the longitudinal axis A and a welding element 18 cooperating with the anvil roller 16. In the example illustrated in FIG. 1, the welding element 18 is a sonotrode of an ultrasonic welding device.

Figure 2:
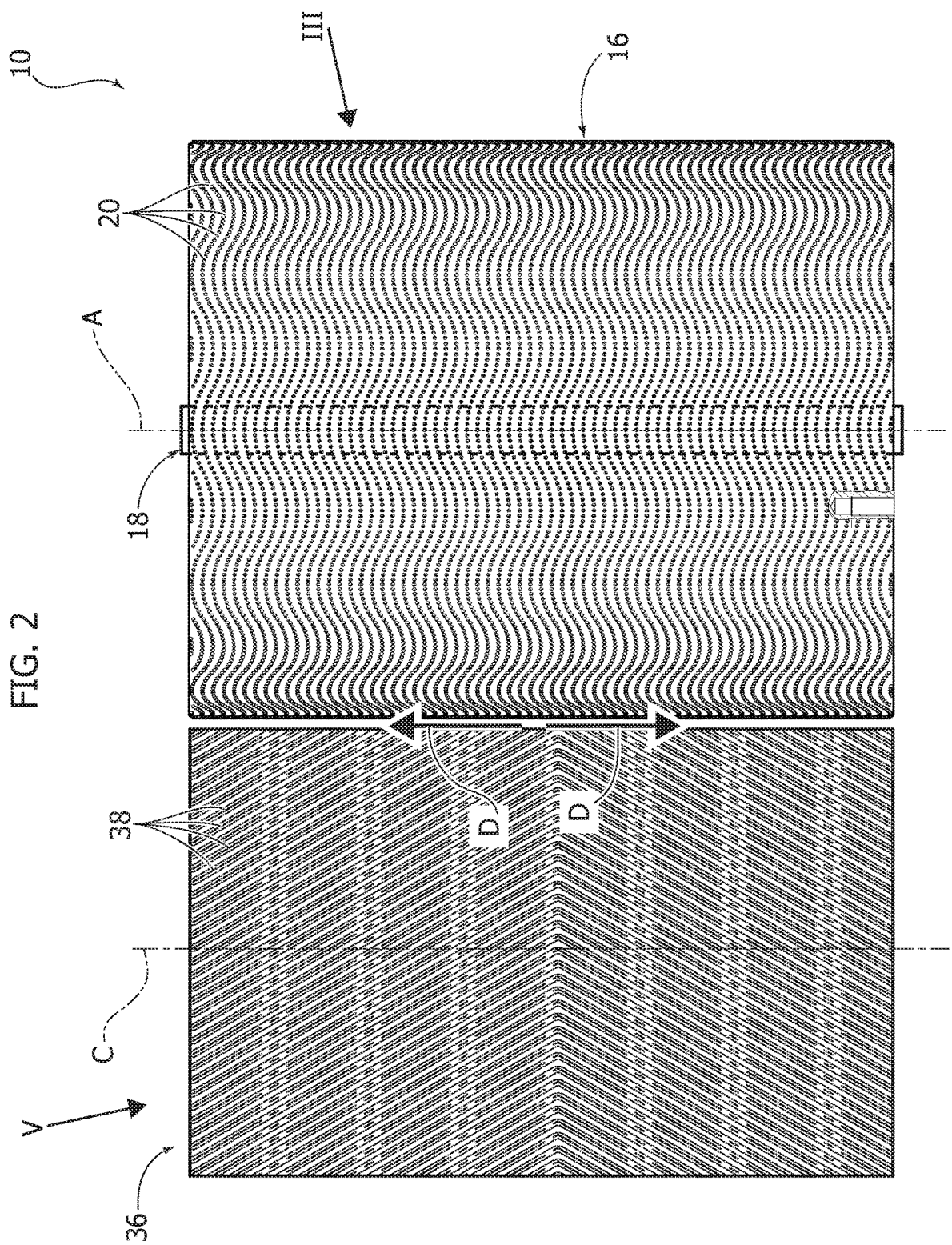
FIG. 2 is a plan view according to the arrow II of FIG. 1.
Figure 3:
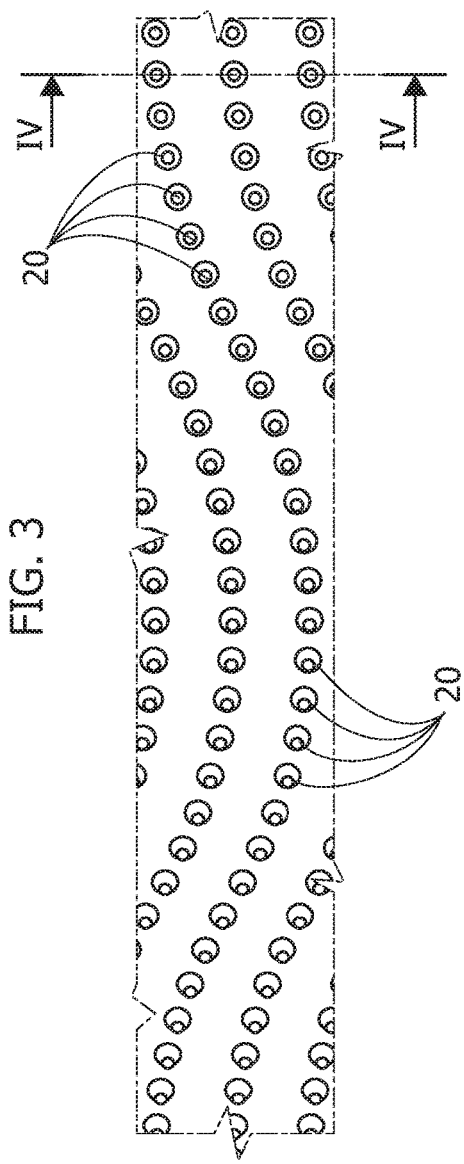
FIG. 3 is a partial view on a larger scale of the part indicated by the arrow III in FIG. 2.
Figure 4:
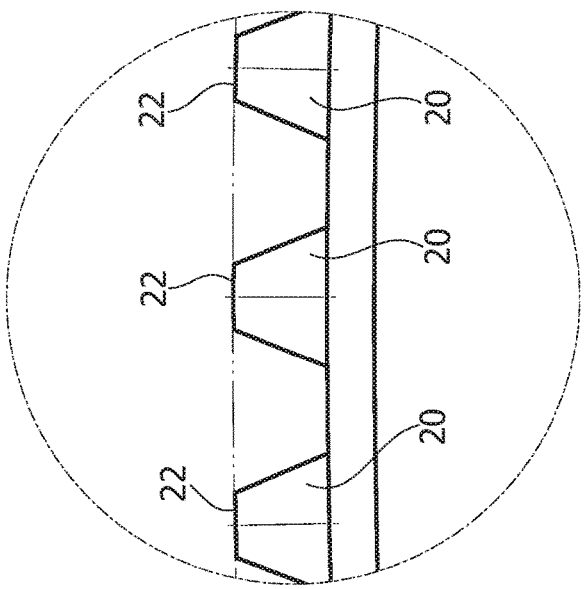
FIG. 4 is a partial cross-section along the line IV-IV of FIG. 3.

With reference to FIGS. 1-4, the outer surface of the anvil roller 16 comprises a plurality of protrusions 20 formed by small pins having head surfaces 22 (FIG. 4) which cooperate with the sonotrode 18 to form ultrasonic welding points on a moving web. The protrusions 20 may have a truncated-conical profile as illustrated in FIG. 4. The head surfaces 22 of the protrusions 20 may have any shape, such as, for example, circular or polygonal (e.g. rhomboidal). The protrusions 20 are arranged on the outer surface of the anvil roller 16 so as to define a welding pattern which corresponds to the distribution of the welding points on the moving web. For example, as shown in FIGS. 2 and 3, the protrusions 20 can be arranged along a series of sinusoidal lines. The shape of the welding pattern may vary according to the desired aesthetic effect on the web surface.

In an alternative embodiment, the welding unit 12 could be a thermo-mechanical welding unit. In this case, the sonotrode 18 would be replaced by a heated welding roller pressed on the outer surface of the anvil roller 16.

The apparatus 10 comprises an inlet roller 24 which guides a composite elastic web W onto the outer surface of the anvil roller 16. The web W is retained on the outer surface of the anvil roller 16 and as a result of the rotation of the anvil roller 16, passes through the welding area 34 formed by the outer surface of the anvil roller 16 and the sonotrode 18 or, alternatively, between the contact surfaces between the anvil roller 16 and the welding roller in the case of thermo-mechanical welding.

The composite web W is formed of a plurality of layers coupled together. In the embodiment illustrated in the figures, the web W is an elastic composite web comprising two layers of non-woven fabric NW1, NW2 and an elastic film EF enclosed between the two layers of fabric NW1, NW2. As already indicated above, the web W could be a single-layer, elastic or non-elastic web.

The apparatus 10 may comprise a feeding assembly 26 arranged to feed the layers that comprise the web W to the inlet roller 24. In the example illustrated in FIG. 1, the feeding assembly 26 may comprise a plurality of pairs of rollers 28, 30, 32 which feed, respectively, the two layers of non-woven fabric NW1, NW2 and the elastic film EF. The rollers 32 that feed the elastic film EF can be controlled to stretch the elastic film EF with respect to its undeformed state. The elastic film EF can be stretched with an elongation in the order of 10-600% and, preferably with an elongation in the order of 50-200%.

The web W is held on the outer surface of the anvil roller 16 and advances in the direction indicated by the arrow B in FIG. 1 at a speed V equal to the peripheral speed of the anvil roller 16. The web W passes through the welding area 34 where the web W is subjected to a welding operation that imparts a spot welding to the web W, with a welding pattern corresponding to the pattern of the protrusions 20.

The apparatus 10 comprises a peeling roller 36, which cooperates with the outer surface of the anvil roller 16 downstream of the welding area 34. The peeling roller 36 is rotatable about an axis C parallel to the rotation axis A of the anvil roller 16. The peeling roller 36 has an outer surface tangent to the outer surface of the anvil roller 16. In particular, the outer surface of the peeling roller 36 is tangent to the head surfaces 22 of the protrusions 20 of the anvil roller 16.

Figure 5:
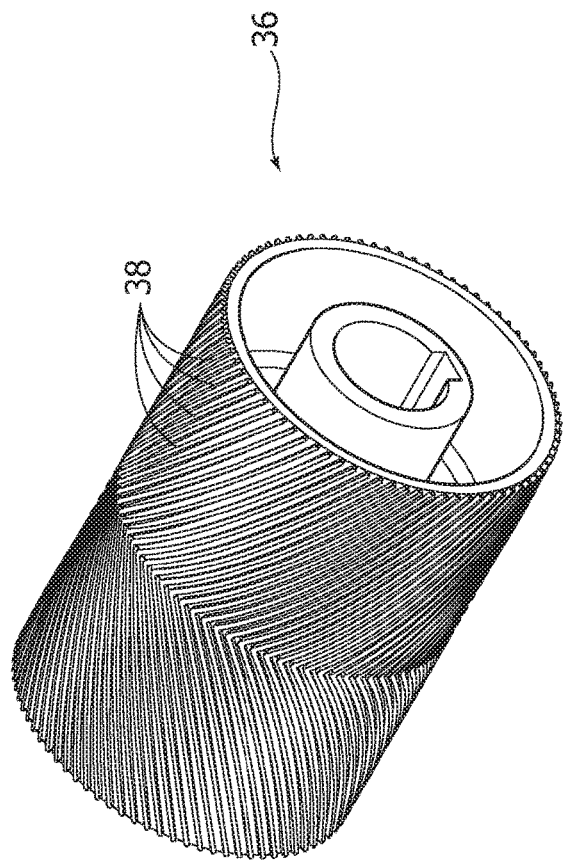
FIG. 5 is a perspective view of a peeling roller indicated by the arrow V in FIG. 2.

As illustrated in FIGS. 2 and 5, the peeling roller 36 has a cylindrical surface on which a plurality of herringbone ribs 38 are formed. The peeling roller 36 is positioned so that the outer surfaces of the ribs 38 are substantially tangent to the head surfaces 22 of the protrusions 20 of the anvil roller 16, preferably with a substantially zero gap. Adjustment systems can be provided which guarantee the correct positioning of the peeling roller 36 with respect to the anvil roller 16. The peeling roller 36 can be kept in contact with the outer surface of the anvil roller 16 with a light contact pressure having the single task of ensuring contact of the peeling roller 36 with the anvil roller 16. A higher contact force between the peeling roller 36 and the anvil roller 16 would not affect the operation of the apparatus 10, but would result in premature wear of the peeling roller 36 and/or the anvil roller 16.

During operation, the peeling roller 36 is driven into rotation about its axis C in a direction consistent with the rotation direction of the anvil roller 16. The peripheral speed V1 of the peeling roller 36 is greater than the peripheral speed V of the anvil roller 16. In one or more embodiments, the peripheral speed V1 of the peeling roller 36 is at least 10% higher than the peripheral speed V of the anvil roller 16.

With reference to FIGS. 2 and 5, the herringbone ribs 38 of the peeling roller 36 have the vertex located at the center of the outer surface of the peeling roller 36. The ribs 38 are spread apart towards the outer sides of the roller 36. With respect to the contact area with the anvil roller 16, the ribs 38 move from the center towards the side edges of the anvil roller 16, as indicated schematically by the arrows D in FIG. 2.

The web W located on the outer surface of the anvil roller 16 passes through the contact area between the peeling roller 36 and the anvil roller 16. The peeling roller 36 acts on the web W after the welding element 18 has carried out the spot welding on the web W.

A release roller 40 is arranged downstream of the peeling roller 36, which detaches the web W from the outer surface of the anvil roller 16.

The apparatus 10 may comprise a waste collecting element 42 located below the contact area between the peeling roller 36 and the anvil roller 16. The waste collecting element 42 can be connected to a suction source.

The web W is at least partly formed of thermoplastic material weldable by means of ultrasonic or thermo-compression welding. In the illustrated example in which the web W comprises an elastic film EF enclosed between two layers of non-woven fabric NW1, NW2, the layers of non-woven fabric comprise thermoplastic fibers (for example, polyester, polypropylene, etc.). The elastic film can be formed of compatible or incompatible material with respect to the thermoplastic fibers of the non-woven layers NW1, NW2. For the purposes of the present description, two materials that can be welded together are considered compatible, while incompatible materials cannot be welded to each other. In the illustrated example, the two layers of non-woven fabric NW1, NW2 are compatible with each other. The elastic film EF can be compatible or incompatible with the material forming the layers of non-woven fabric NW1, NW2.

Figure 6:
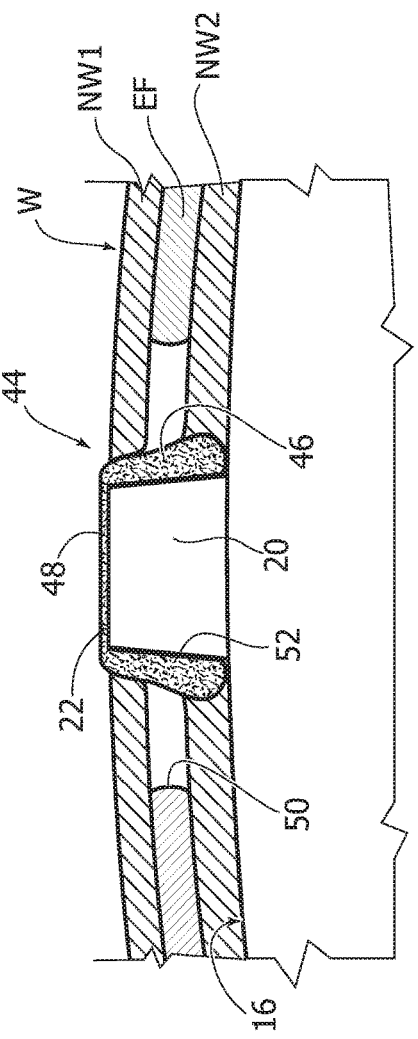

FIG. 6 shows a very enlarged transverse section of a welding point on the web W in the portion downstream of the welding area 34 and upstream of the peeling roller 36. The web W is compressed between the welding element 18 and the head surfaces 22 of the protrusions 20 of the anvil roller 16. Following this compression, localized melting of the thermoplastic material is obtained around the protrusions 20. A plurality of welding points 44 are formed on the web W at respective protrusions 20, downstream of the welding area 34. Each welding point 44 comprises an annular welding seam 46 which extends around the respective protrusion 20, and a thin membrane 48 which extends within the annular welding seam 46 at the head surface 22 of the respective protrusion 20. The annular welding seam 46 and the thin membrane 48 are formed of melted thermoplastic material. The thin membrane 48 may have a thickness in the order of 0.01 mm. In the example illustrated in FIG. 6, the two layers of non-woven fabric NW1, NW2 are welded together at each welding point 44 by means of the annular welding seam 46. In the example of FIG. 6, the elastic film EF is made of a material that is incompatible with the materials forming the non-woven layers NW1, NW2. Therefore, in this case, the weld forms a through-hole 50 through the elastic film EF. In this case, the elastic film EF is not welded to the non-woven layers NW1, NW2. In the case in which the elastic film EF is made of a material compatible with the material forming the non-woven layers NW1, NW2, the elastic film EF is welded to the annular welding seam 46 (FIG. 9).

Downstream of the welding step, the web W is subjected to an operation for removing the thin membranes 48 formed at the welding points 44. Removal of the thin membranes 48 is carried out while the welding points 44 are engaged on the respective protrusions 20 of the anvil roller 16.

The removal operation of the thin membranes 48 is carried out by passing the web W through the contact area between the peeling roller 36 and the anvil roller 16.

Figure 7:
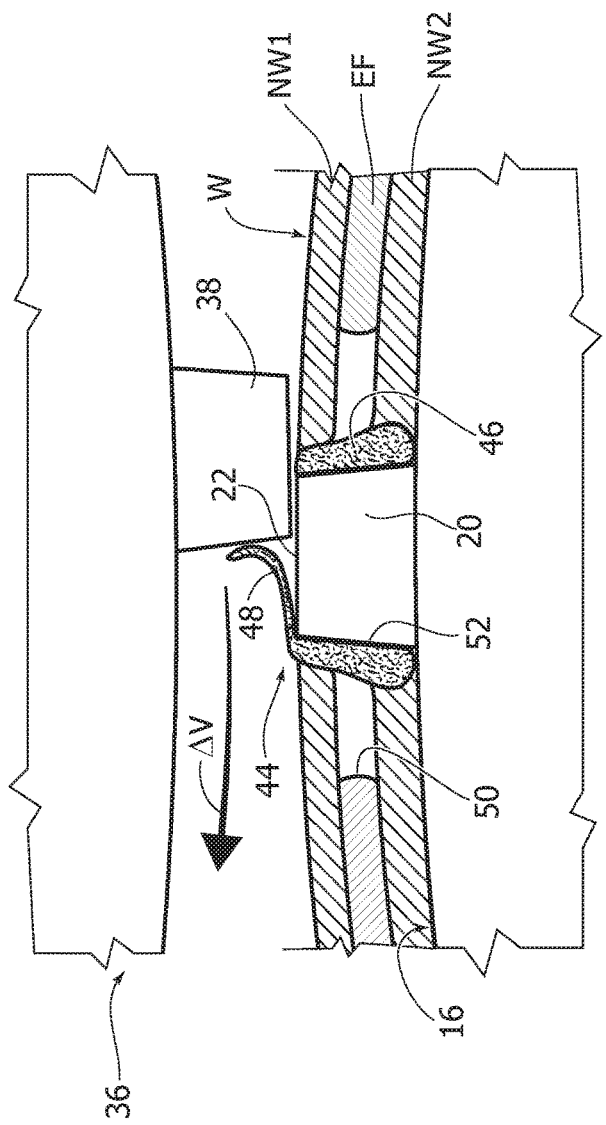

As illustrated in FIG. 7, the ribs 38 of the peeling roller 36 move relative to the head surfaces 22 of the protrusions 20 with a velocity $\Delta V = V1 - V$, where V1 and V are the peripheral speeds of the peeling roller 36 and the anvil roller 16, respectively. The ribs 38 of the peeling roller 36 remove the thin membranes 48 as illustrated in FIG. 7. The thin membranes 48 are removed with a cutting or abrasion action, due to the fact that the mutually facing surfaces of the protrusions 20 and of the ribs 38 are spaced apart from each other by a distance less than the thickness of the membranes 48, and are provided with a relative movement. The herringbone conformation of the ribs 38 of the peeling roller 36 ensures that, at the protrusions 20, the ribs 38 have a relative movement directed towards the edges of the web W. This ensures that the web is held firmly on the surface of the anvil roller 16 and wrinkling or unwinding of the web W is avoided. The thin membranes 48 removed by the peeling roller 36 are collected by the waste collecting element 42 located below the contact area between the peeling roller 36 and the anvil roller 16, and are drawn into a waste collecting container.

Downstream of the peeling roller 36, the web W is detached from the surface of the anvil roller 16 by means of the release roller 40.

Downstream of the release roller 40, the web W—at the welding points 44—has the structure schematically represented in FIG. 8. The web W has a plurality of welding points 44, each of which is formed by an annular welding seam 46 of thermoplastic material obtained from the local melting of the fibers of the non-woven layers NW1, NW2. The web W has a plurality of through-holes 52 inside the respective annular welding seams 46. The elastic film EF has a through-hole 50 surrounding the annular crown 46. The through-holes 52 allow the passage of air through the web W and confer high breathability characteristics to the web W. The web W also has breathable areas in the annular space between the hole 50 of the elastic film EF and the annular welding seam 46 of each welding point 44. In these areas, the breathability of the web W is given by the porosity of the non-woven layers NW1, NW2.

FIG. 9 illustrates a variant in which the film of elastic material EF is made of a compatible material (therefore weldable) with the materials forming the non-woven layers NW1, NW2. In this case, at the welding points 44, the elastic film EF is welded to the annular welding seam 46. In this case, the breathability of the web W is only given by the through-holes 52 inside the respective annular welding seams 46.

The apparatus and the method according to the present invention can be used with an ultrasonic welding unit or a thermo-mechanical welding unit, and with any shape or geometry of the welding pattern. The apparatus and the method according to the present invention allow a breathable composite elastic web to be obtained in the case of three-layer elastic webs in which the elastic film would make the web non-breathable.

Of course, without prejudice to the principle of the invention, the details of construction and the embodiments may be widely varied with respect to those described and illustrated, without thereby departing from the scope of the invention as defined by the claims that follow.

The invention claimed is:

1. A method for producing a breathable web, comprising:
   feeding a web on the surface of an anvil roller rotatable about its axis and having a plurality of welding protrusions cooperating with a welding element;
   welding said web at a plurality of welding spots on head surfaces of said welding protrusions and forming respective annular welding seams at said welding spots, about respective welding projections, and respective thin membranes located within said annular welding seams and adjacent to the head surfaces of said welding protrusions; and
   removing said thin membranes after said welding by means of a peeling roller having an outer surface tangent to said head surfaces of said welding protrusions.

2. A method according to claim 1, wherein said peeling roller is rotatable about an axis parallel to the rotation axis of said anvil roller.

3. A method according to claim 1, wherein said peeling roller is rotatable about its axis in a direction concordant to the rotational direction of the anvil roller.

4. A method according to claim 1, wherein said peeling roller has a peripheral velocity greater than the peripheral velocity of the anvil roller.

5. A method according to claim 4, wherein the peripheral velocity of said peeling roller is at least 10% greater than the peripheral velocity of the anvil roller.

6. A method according to claim 1, wherein said peeling roller has a plurality of herringbone ribs on its outer surface having a relative movement from the inside outwards with respect to the head surfaces of said welding projections of the anvil roller.

* * * * *